(12) United States Patent
Hoffmann

(10) Patent No.: US 9,090,926 B2
(45) Date of Patent: Jul. 28, 2015

(54) METHOD FOR CELL LYSIS AND PCR WITHIN THE SAME REACTION CHAMBER

(71) Applicant: Roche Diagnostics Operations, Inc., Indianapolis, IN (US)

(72) Inventor: Ingrid Hoffmann, Bad Heilbrunn (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 124 days.

(21) Appl. No.: 13/853,830

(22) Filed: Mar. 29, 2013

(65) Prior Publication Data

US 2013/0203120 A1    Aug. 8, 2013

Related U.S. Application Data

(63) Continuation of application No. PCT/EP2011/067068, filed on Sep. 30, 2011.

(30) Foreign Application Priority Data

Oct. 4, 2010   (EP) .................................. 10186417

(51) Int. Cl.
*C12P 19/34* (2006.01)
*C12Q 1/68* (2006.01)

(52) U.S. Cl.
CPC ............... *C12P 19/34* (2013.01); *C12Q 1/6851* (2013.01)

(58) Field of Classification Search
CPC ........... C12Q 1/6851; C12Q 2547/101; C12Q 2549/101; C12Q 2521/107; C12Q 2561/113; C12P 19/34

See application file for complete search history.

(56) References Cited

U.S. PATENT DOCUMENTS

2011/0223653 A1* 9/2011 Chakrabarty ............... 435/287.2
2011/0287951 A1* 11/2011 Emmert-Buck et al. .......... 506/7

FOREIGN PATENT DOCUMENTS

WO    2007076493 A2    7/2007
WO    2010040831 A1    4/2010

* cited by examiner

*Primary Examiner* — Cynthia B Wilder
(74) *Attorney, Agent, or Firm* — David J. Chang

(57) ABSTRACT

A method for amplification of a target DNA, comprising the steps of (i) transferring a liquid with a first volume comprising at least one or more living cells into a vessel (ii) adding to said vessel a PCR reaction buffer with a second volume, whereas said second volume is at least 2× as large as said first volume (iii) lysing said at least one or more living cells within said vessel by means of incubation for at least 1 Minute at at least 90° C., and (iv) amplifying said target by means of a polymerase chain reaction without performance of an intermediate purification step.

14 Claims, No Drawings

US 9,090,926 B2

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: forward primer

<400> SEQUENCE: 1
agcttgtcat caacgggaag                                                   20

<210> SEQ ID NO 2
<211> LENGTH: 21
<212> TYPE: DNA
<213> ORGANISM: Artificial Sequence
<220> FEATURE:
<223> OTHER INFORMATION: reverse primer

<400> SEQUENCE: 2
tttgatgtta gtggggtctc g                                                 21

<210> SEQ ID NO 3
<211> LENGTH: 20
<212> TYPE: DNA
<213> ORGANISM: Artificial Sequence
<220> FEATURE:
<223> OTHER INFORMATION: forward primer

<400> SEQUENCE: 3
catgaggtcg ggtggaagta                                                   20

<210> SEQ ID NO 4
<211> LENGTH: 20
<212> TYPE: DNA
<213> ORGANISM: Artificial Sequence
```

```
<220> FEATURE:
<223> OTHER INFORMATION: reverse primer

<400> SEQUENCE: 4
gcctgtttcc gtaacctcaa                                              20

<210> SEQ ID NO 5
<211> LENGTH: 20
<212> TYPE: DNA
<213> ORGANISM: Artificial Sequence
<220> FEATURE:
<223> OTHER INFORMATION: forward primer

<400> SEQUENCE: 5
ctgtcttgcc ttcgtgctct                                              20

<210> SEQ ID NO 6
<211> LENGTH: 20
<212> TYPE: DNA
<213> ORGANISM: Artificial Sequence
<220> FEATURE:
<223> OTHER INFORMATION: reverse primer

<400> SEQUENCE: 6
agcagggcta tcaaccaaaa                                              20

<210> SEQ ID NO 7
<211> LENGTH: 20
<212> TYPE: DNA
<213> ORGANISM: Artificial Sequence
<220> FEATURE:
<223> OTHER INFORMATION: forward primer

<400> SEQUENCE: 7
aaggccaacc gtgaaaagat                                              20

<210> SEQ ID NO 8
<211> LENGTH: 21
<212> TYPE: DNA
<213> ORGANISM: Artificial Sequence
<220> FEATURE:
<223> OTHER INFORMATION: reverse primer

<400> SEQUENCE: 8
gtggtacgac cagaggcata c                                            21

<210> SEQ ID NO 9
<211> LENGTH: 20
<212> TYPE: DNA
<213> ORGANISM: Artificial Sequence
<220> FEATURE:
<223> OTHER INFORMATION: forward primer

<400> SEQUENCE: 9
tacgcctgca gagttaagca                                              20

<210> SEQ ID NO 10
<211> LENGTH: 23
<212> TYPE: DNA
<213> ORGANISM: Artificial Sequence
<220> FEATURE:
<223> OTHER INFORMATION: reverse primer

<400> SEQUENCE: 10
ggttcaaatg aatcttcaga gca                                          23
```

```
<210> SEQ ID NO 11
<211> LENGTH: 21
<212> TYPE: DNA
<213> ORGANISM: Artificial Sequence
<220> FEATURE:
<223> OTHER INFORMATION: forward primer

<400> SEQUENCE: 11
gccgctagag gtgaaattct t                                              21

<210> SEQ ID NO 12
<211> LENGTH: 19
<212> TYPE: DNA
<213> ORGANISM: Artificial Sequence
<220> FEATURE:
<223> OTHER INFORMATION: reverse primer

<400> SEQUENCE: 12
cgtcttcgaa cctccgact                                                 19
```

METHOD FOR CELL LYSIS AND PCR WITHIN THE SAME REACTION CHAMBER

CROSS-REFERENCE TO RELATED APPLICATIONS

This application is a continuation of International Application No. PCT/EP2011/067068, filed Sep. 30, 2011, which claims the benefit of European Patent Application No. 10186417.1, filed Oct. 4, 2010, the disclosures of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Mar. 22, 2013, is named 27058US_SEQ_LISTING.txt, and is two thousand five-hundred and nineteen bytes in size.

BACKGROUND OF THE DISCLOSURE

PCR enables exponential amplification of nucleic acids. In particular real time PCR (a.k.a., qPCR) enables simultaneous analysis of the amplified nucleic acid during amplification, for example by means of melting curve analysis.

Automation of PCR (for example, in conjunction with qPCR systems) has also made significant progress, further enabling performance of 96, 384 or 1536 PCR reactions, for example in microtiter plate formats. Such systems are also becoming more user friendly. For example, microtiter plates comprising the compounds necessary to perform PCR amplification and/or detection (e.g., in freeze dried form) are commercially available. Nevertheless, it remains a challenge to further improve the work flow for PCR analysis, in particular, for automatable high throughput PCR analysis allowing for simplified DNA analysis.

BRIEF SUMMARY OF THE DISCLOSURE

The instant disclosure provides new methods and systems for performing DNA analysis from minute starting material such as only a few cells, and subsequent direct analysis of said sample nucleic acid by means of real time PCR. The systems and methods herein provide an improved and automatable high throughput method which allows for a further simplified nucleic acid, such as DNA, analysis protocol.

The present disclosure provides a method for amplification of a target nucleic acid, comprising the steps of transferring a liquid sample with a first volume comprising one or more living cells into a vessel, adding to said vessel a PCR reaction buffer with a second volume, whereas said second volume is at least 2× as large as said first volume, lysing said one or more living cells within said vessel by means of incubation for at least 30 seconds at at least 90° C., and amplifying said target by means of a polymerase chain reaction with a thermostable DNA polymerase without performance of an intermediate purification step. Such methods are characterized in that the transferring to amplifying steps are performed within the same vessel.

According to some embodiments, the lysing step takes at least 1 minute. In some embodiments, the vessel may be, for example a well of a microtiter plate. Said vessel of said microtiter plate may comprise a dry composition of PCR amplification primers. Furthermore, said dry composition may comprise either at least one labeled hybridization probe or a double strand DNA binding fluorescent compound. In addition, said dried composition may additionally comprise a thermostable DNA polymerase and dNTPs. Alternatively, in some embodiments, said vessel may be a capillary or a tube of a stripe of reaction tubes.

In some embodiments of the instant disclosure, said liquid sample comprising at least one or more living cells may have been gained by a cell sorting method prior to step the step of transferring. In some embodiments, the ratio of the number of said living cells of the transferring step versus the liquid volume in which the polymerase chain reaction of the amplifying step is performed is not greater than 2 cells/μl. Further, in some embodiments, the target DNA may be a single copy DNA.

In other aspects of the present disclosure, a kit comprising a plurality of reaction vessels designed to fit into a thermocycler instrument is provided. Said kit also comprises PCR reaction buffer comprising a thermostable DNA polymerase capable of performing PCR and dNTPs. According to some embodiments, the plurality of reaction vessels may be physically connected with each other in a form of a microtiter plate or a linear strip of reaction vessels. Additionally, in some embodiments, said reaction vessels may comprise a dry composition of at least one pair of PCR amplification primers and optionally either at least one labeled hybridization probe or a double strand DNA binding fluorescent compound.

In yet further embodiments of the instant disclosure, a method of amplifying a target nucleic acid within a liquid sample is provided. Embodiments of such method include the steps of transferring the liquid sample comprising one or more living cells comprising the target nucleic acid into a vessel, the liquid sample having a first volume; adding a PCR reaction buffer having a second volume to the vessel, the second volume being at least two times as large as the first volume; incubating the vessel for at least 30 seconds at at least 90° C.; and amplifying the target nucleic acid by means of a polymerase chain reaction with a thermostable DNA polymerase, said step of amplifying occurring without performance of an intermediate purification step following said step of incubating, and said steps of transferring, adding, incubating and amplifying being performed within the same vessel. In some embodiments, the vessel is a well of a microtiter plate. In some such embodiments the well of the microtiter plate comprises a dry composition of PCR amplification primers. In some embodiments thereof, the dry composition further comprises one of a labeled hybridization probe and a double strand DNA binding fluorescent compound.

In further embodiments, the liquid sample is subjected to a cell sorting method prior to said step of transferring. In even further embodiments, the living cells of said step of transferring comprise a ratio, in comparison to a volume in which the polymerase chain reaction of said step of amplifying is performed, of not greater than 2 cells/μl. In some such embodiments, the ratio is at least 1 cell/25 μl. In even further embodiments, the thermostable DNA polymerase is configured to become activated during said step of incubating. In some such embodiments, the thermostable DNA polymerase comprises a chemical modification which is removed during said step of incubating.

In even further embodiments of the instant disclosure, a kit is disclosed comprising a plurality of reaction vessels configured to fit into a thermocycler instrument; and a PCR reaction buffer having a thermostable DNA polymerase and dNTPs. According to some embodiments, the plurality of reaction vessels include a dry composition having a pair of PCR amplification primers and one of a labeled hybridization probe and a double strand DNA binding fluorescent compound. In some such embodiments, the pair of PCR amplification primers are designed to amplify a single copy gene.

DETAILED DESCRIPTION OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

Generally speaking, the present disclosure provides methods and systems which enable lysis of a cell sample in a liquid environment that may be used directly for nucleic analysis by means of applying the Polymerase Chain reaction without any intermediate purification step or complex liquid handling procedures. An embodiment of the present disclosure provides a method for amplification of a target nucleic acid, comprising the steps of:

a) transferring a liquid sample with a first volume comprising one or more living cells into a vessel;
b) adding to said vessel a PCR reaction buffer with a second volume, whereas said second volume is at least 2× as large as said first volume;
c) lysing said one or more living cells within said vessel by means of incubation for at least 30 seconds at at least 90° C.; and
d) amplifying said target nucleic acid by means of a polymerase chain reaction with a thermostable DNA polymerase without performance of an intermediate purification step.

According to an aspect of the present disclosure it is possible that all steps (e.g., a), b), c) and d)) may be performed within the same reaction vessel.

The target nucleic acid may be DNA, i.e. a specific part of the genomic DNA. In such embodiments, the polymerase chain reaction may be carried out with a DNA dependent DNA Polymerase such as Taq DNA polymerase or the like. The specific part of the DNA may be amplified in order to identify any type of genomic variations such as single nucleotide polymorphisms and the like.

As demonstrated by the examples provided herein, the present disclosure provides methods which are surprisingly applicable for performing a PCR analysis starting from only one single living cell as the original sample material. Moreover, the present disclosure surprisingly makes it possible to reproducibly amplify and analyze target DNA from a single copy gene from only a few cells or even one single cell.

Furthermore, the target nucleic acid of embodiments of the present disclosure may also be RNA for the purpose of monitoring respective RNA expression levels. In such embodiments, an RT-PCR reaction may be performed. According to some such embodiments, the target nucleic acid is amplified with a thermostable polymerase that comprises both RNA template dependent polymerase activity (Reverse Transcriptase activity) and DNA template dependent activity. Exemplary enzymes include Tth DNA polymerase (Roche Applied Science Cat. No: 11 480 022 001) and the C. therm Polymerase system (Roche Applied Science Cat. No: 12 016 346 001), for example.

According to an embodiment of the instant disclosure, a method for amplification of a target nucleic acid is provided. Embodiments of the method comprise the steps of:

a) transferring a liquid sample with a first volume comprising one or more living cells into a vessel;
b) adding to said vessel a PCR reaction buffer with a second volume, whereas said second volume is at least 2× as large as said first volume;
c) lysing said one or more living cells within said vessel by means of incubation for at least 30 seconds at at least 90° C.; and
d) amplifying said target nucleic acid by means of a polymerase chain reaction with a thermostable DNA polymerase without performance of an intermediate purification step.

Step a)

The one or more living cells according to step a) of the method above, in some embodiments, are eukaryotic cells of human, animal or plant origin. The cells may be derived from cell lines or biopsies, for example.

The liquid containing the cells may be any liquid, blood buffer or medium in which said cells survive for at least a certain period of time, which is preferably longer than 30 minutes. Such a liquid, for example may be a medium in which cells living and growing in suspension have been successfully cultivated. In case of adherent cells, the liquid may be a buffer, in which the cells have been detached from the solid support. In some embodiments, such a buffer is free of any proteases which might have an inhibitory effect on the subsequent polymerase mediated PCR amplification reaction. Such an effect, if observed, may be avoided by subjecting the cells to an additional washing step prior to deposition into the vessel.

The transfer of the liquid into the vessel may be achieved either manually by means of first preparing an appropriate dilution series of a cell sample and then pipetting an equivalent of only one or several cells into said vessel. In some embodiments, the transfer is achieved using an appropriate automated pipetting station or, in some cases, a cell sorter. Such cell sorting machines are commercially available from various manufacturers. Due to the underlying technology of cell sorters, from time to time large particles from cell debris may be mistakenly recognized by the cell sorters as cells. Due to this effect, in case of single cell analysis, some samples may give no results during the subsequent PCR reaction.

According to some embodiments of the instant disclosure, the number of cells transferred to the reaction vessel should be limited since without any purification step, the presence of cellular debris in higher concentrations may inhibit subsequent PCR amplification. Advantageously, the number of cells transferred to the reaction vessel may be adjusted so that step d) (of the embodiment set forth above and discussed in more detail below) is performed in such a way that the sample does not exceed a ratio of 2 cell equivalents/µl.

Also according to some embodiments, the number of cells transferred to the reaction vessel should not be too low, because otherwise it may become difficult to perform a PCR reaction for the amplification of single copy genes. In some embodiments, the number of cells transferred to the reaction vessel may be adjusted so that step d) is performed in such a way that the sample comprises a ratio of at least 1 cell equivalents/25 µl.

The volume of the liquid is sufficiently small such that addition of the PCR reaction buffer in step b) (of the embodiment set forth above and discussed in more detail below) and—if required—addition of further compounds required for the subsequent PCR reaction finally result in a final volume which is still reasonably small for performance of said PCR. Said volume should in general not exceed 100 and/or 200 µl. Advantageously, said volume, according to some embodiments, is not more than 50 µl. In some embodiments, volumes of 20 µl or less, and even 10 µl are used. In case of automated deposition of the liquid containing the one or more cells can be very low in sub-μl range. In particular, if a cell sorter is used, a volume containing only one cell equivalent may be about less than 100 nl. Even if in the latter case the sample is dried out, it has been proven by the inventors of the instant disclosure that the new method is still effective. In an exemplary embodiment of single cell analysis, the final volume does not exceed 25 μl. This embodiment still allows for efficient single copy gene amplification.

The reaction vessel may be any type of reaction vessel, in which a PCR reaction can be performed. For example, according to the instant disclosure the vessel has sufficient heat resistance for the PCR thermocycling protocol where it is repeatedly exposed to high temperatures of 90° C. or above.

In an exemplary embodiment, the reaction vessel comprises a well of a microtiter plate which may be placed into a thermocycler instrument. This allows to execute the method of the present disclosure on a number of samples in a highly parallel manner. Microtiter plates comprising 24, 96, 384, and 1536 wells are known in the art and commercially available from a multitude of different suppliers. Microtiter plates available in the art allow for reaction volumes of at least 2 μl. Such microtiter plates can be subjected to high temperature of at least 90° C. by means of placing them on an appropriate heating block, or, alternatively, directly into a PCR Thermocycler instrument which is designed to incorporate microtiter plates.

In an additional illustrative embodiment, the reaction vessel may be a single reaction tube or a reaction tube which is a part of a strip of reaction tubes that are connected to each other so that they can jointly be placed into the heating block of a thermocycler instrument. In a further embodiment, the reaction vessel is a specific capillary which can be placed into a capillary LightCycler instrument (Roche Applied Science Cat. No. 023 531 414 001).

Step b)

In the context of the present disclosure, the term "PCR reaction buffer" which may be added at step b) of the present disclosure is understood as any liquid in which the sample later on can be subjected to a PCR reaction without any intermediate purification step. The said second volume of the PCR reaction buffer added, according to some embodiments, may be at least twice (2×) as large and in some embodiments 5 times (5×) as large as the first volume. This will allow for efficient amplification of the target nucleic acid during the subsequent PCR reaction.

In some embodiments, the "PCR reaction buffer" already contains all compounds which are required for the performance of a PCR reaction, which are a thermostable DNA polymerase, a mixture of deoxynucleoside-triphosphates (dNTPs), The "PCR reaction buffer" may also comprise an appropriate pH buffering compound (e.g. Tris), a Mg2+ salt, a hot start component and the like.

In further embodiments, the "PCR reaction buffer" may also comprise at least one appropriate pair of amplification primers. In an illustrative embodiment, the "PCR reaction buffer" may in addition already comprise compounds that are required for monitoring the amplification of the target DNA in real time. In particular, these compounds may comprise fluorescent hybridization probes or a double stranded DNA binding dye, for example. The specifics of various possible detection formats are discussed below.

It is also within the scope of the disclosure, if some, any or all of the aforementioned components or any other additional compounds are added subsequent to lysis, but prior to the performance of the actual amplification reaction. Thus the present disclosure also explicitly encompasses an embodiment, wherein the "PCR reaction buffer" according to meaning as used in the context of the present disclosure is simply water.

Step c)

According to the present disclosure, lysis of the cells takes place within the PCR reaction buffer, without any prior addition of a specific lysis step reagent conventionally used in the art. Rather, lysis of the one or more living cells takes place by means of incubating the sample for a period of at least 60 seconds at at least 90° C. Usually, according to the instant disclosure, a period of 30 seconds of high temperature incubation will be sufficient for a complete lysis of a moderate number of cells (not more than 64 cells) which enables for subsequent amplification and detection of single copy genes. However, it is also within the scope of the present disclosure, if said period is prolonged up to a period of 30 minutes. However, periods of less than 15 and/or 3 minutes are suggested according to some embodiments of the disclosure.

According to various embodiments, the temperature used for cell lysis does not exceed 100° C. and in most cases does not exceed 95° C. because, at higher temperatures, there is an increasing risk that the components contained in the reaction buffer which are required for the subsequent PCR reaction are destroyed. For example, even thermostable DNA polymerases such as Taq DNA polymerase may become substantially denatured or degraded at temperatures above 100° C.

Step d)

As evidenced by the examples provided herein, a PCR reaction can be performed using the lysate directly without intermediate purification step. Dependent on the embodiment, however it is within the scope of the present disclosure, if additional compounds required for said PCR reaction are added to the sample subsequent to the lysis.

Since the present disclosure is applicable for analysis nucleic acids originating from only very few or even single cells, it is advantageous for the design of an experiment according to the present disclosure, if consideration is given to the ratio between the number of cells analyzed and the volume in which the actual PCR reaction according to step d) (of the embodiments set forth above and discussed in more detail below) takes place. On the one hand, the PCR reaction should be performed in a minimal volume in order to achieve an optimal degree of sensitivity if such a low amount of starting material shall be analyzed. According to illustrative embodiments of the instant disclosure, it has been shown that a ratio of the number of said cells of step a), versus the liquid volume in which the polymerase chain reaction of step d) is performed, of at least 1 cell/20 μl PCR reaction volume is advantageous.

Also, since there is no intermediate purification step, the lysed sample will contain cellular debris which may interfere with the efficiency of the PCR reaction. According to some illustrative embodiments of the instant disclosure, it has been shown that a ratio of the number of said living cells or cell equivalents of step a), versus the liquid volume in which the polymerase chain reaction of step d) is performed, of not greater than 2 cells/μl is advantageous. Further, a ratio between 1 cell/25 μl and 2 cells/μl has also been shown to be advantageous. As disclosed herein, a ratio within this range enables single copy analysis on DNA originating from only 1 single cell as well as a much higher cell numbers.

The PCR reaction may be a conventional PCR reaction, wherein the set comprises the target DNA, dNTPs, DNA Polymerase, which may be a DNA dependent DNA polymerase, an appropriate pH buffering system such as Tris and some other accessory compounds such as Mg2+ salts and the like. In some embodiments, the Polymerase may also be a thermostable DNA Polymerase which is also capable of performing 1-step RT PCR in order to use the inventive method for monitoring of gene expression.

Analysis of the amplified DNA may be subsequently achieved usually by means of Gel Electrophoresis. However, in some embodiments, the PCR reaction may be a real time PCR reaction, wherein the progress of amplification is continuously monitored using, for example any of the following detection formats which are generally describe herein.

TaqMan Hydrolysis Probe Format:

A single-stranded Hybridization Probe is labeled with two components. When the first component is excited with light of a suitable wavelength, the absorbed energy is transferred to the second component, the so-called quencher, according to the principle of fluorescence resonance energy transfer. During the annealing step of the PCR reaction, the hybridization probe binds to the target DNA and is degraded by the 5'-3' exonuclease activity of the Taq Polymerase during the subsequent elongation phase. As a result the excited fluorescent component and the quencher are spatially separated from one another and thus a fluorescence emission of the first component can be measured. TaqMan probe assays are disclosed in detail in U.S. Pat. No. 5,210,015, U.S. Pat. No. 5,538,848, and U.S. Pat. No. 5,487,972, for example. TaqMan hybridization probes and compound mixtures are disclosed in U.S. Pat. No. 5,804,375, for example. In some embodiments, the Taqman hybridization probes may comprise UPL probes from the Universal Probe Library as available from Roche Applied Sciences (Cat. 2010/2011, p. 577).

Molecular Beacons:

These hybridization probes are also labeled with a first component and with a quencher, the labels generally being located at both ends of the probe. As a result of the secondary structure of the probe, both components are in spatial vicinity in solution. After hybridization to the target nucleic acids both components are separated from one another such that after excitation with light of a suitable wavelength the fluorescence emission of the first component can be measured (U.S. Pat. No. 5,118,801).

FRET Hybridization Probes:

The FRET Hybridization Probe test format is useful for homogenous hybridization assays (Matthews, J. A., and Kricka, L. J., Analytical Biochemistry 169 (1988) 1-25). It is characterized by two single-stranded hybridization probes which are used simultaneously and are complementary to adjacent sites of the same strand of the amplified target nucleic acid. Both probes are labeled with different fluorescent components. When excited with light of a suitable wavelength, a first component transfers the absorbed energy to the second component according to the principle of fluorescence resonance energy transfer such that a fluorescence emission of the second component can be measured when both hybridization probes bind to adjacent positions of the target molecule to be detected. Alternatively to monitoring the increase in fluorescence of the FRET acceptor component, it is also possible to monitor fluorescence decrease of the FRET donor component as a quantitative measurement of hybridization event.

In particular, the FRET Hybridization Probe format may be used in real time PCR, in order to detect the amplified target DNA. As an alternative to the usage of two FRET hybridization probes, it is also possible to use a fluorescent-labeled primer and only one labeled oligonucleotide probe (Bernard, P. S., et al., Analytical Biochemistry 255 (1998) 101-107). In this regard, it may be chosen arbitrarily, whether the primer is labeled with the FRET donor or the FRET acceptor compound.

Double Strand DNA Binding Dye Format:

It is also within the scope of the disclosure, if real time PCR is performed in the presence of an additive according to the disclosure in case the amplification product is detected using a double stranded nucleic acid binding moiety. For example, the respective amplification product can also be detected according to the disclosure by a fluorescent DNA binding dye which emits a corresponding fluorescence signal upon interaction with the double-stranded nucleic acid after excitation with light of a suitable wavelength. The dyes SybrGreenI and SybrGold (Molecular Probes), for example, are known in the art. Another exemplary dye is the LightCycler 480 Resolight dye (Roche Applied Science Cat. No: 04 909 640 001).

Melting Curve Analysis:

Due to the fact that real time amplicon detection with SybrGreen format cannot discriminate between specific products and amplification artifacts such as primer/dimers, a subsequent melting curve analysis may be performed. After completion of the PCR-reaction, the temperature of the sample is constitutively increased, and fluorescence is detected as long as SybrGreen is bound to the double stranded DNA present in the samples. Upon dissociation of the double stranded DNA the signal decreases immediately. This decrease is monitored with an appropriate fluorescence versus temperature-time plot such that a first derivative value can be determined, at which the maximum of fluorescence decrease is observed. Since primer/dimer double stranded DNAs are usually short, dissociation into single stranded DNA occurs at lower temperatures as compared to the dissociation of the double stranded specific amplification product.

Moreover, also Molecular Beacons and FRET hybridization probes are used for melting curve analysis. After completion of the PCR-reaction, the temperature of the sample is constitutively increased, and fluorescence is detected as long as the hybridization probes are bound to the target DNA. At melting temperature, the hybridization probes are released from their target, and the fluorescent signal is decreasing immediately down to the background level. This decrease is monitored with an appropriate fluorescence versus temperature-time plot such that a first derivative value can be determined, at which the maximum of fluorescence decrease is observed.

Hot Start PCR:

The PCR reaction set up may contain some compounds which are providing a hot start effect, i.e. the inhibition of unspecific primer annealing and subsequent elongation at ambient temperature, which occasionally results in unspecific amplification products such as primer dimer formation. Upon temperature increase, this inhibition is reduced or eliminated due to release of the hot start compound from any binding partner with the consequence that the thermostable DNA Polymerase is becoming thermally activated and specific polymerase catalyzed primer extension can occur. Examples for such compounds are known in the art. A specific example is given in U.S. Pat. No. 5,338,671, which discloses a Taq Polymerase antibody as a hot start compound. More recent examples for such hot start compounds are disclosed in EP 1 989 324 A and EP 2 163 556.

Said hot start compounds may be added to the sample subsequent to lysis together with the polymerase and any other PCR compounds prior to step d). In some embodiments, the hot start compounds may be included already within the "PCR reaction buffer" that is being added during step b). As a consequence the thermal activation of the thermostable DNA polymerase can already be achieved through the incubation at at least 90° C. during step c).

In some embodiment, the DNA polymerase is reversibly inactivated as a result of a chemical modification. More precisely, heat labile blocking groups are introduced into the Taq DNA polymerase which renders the enzyme inactive at room temperature. These blocking groups are removed at high temperature during a pre-PCR step such that the enzyme becomes activated. Such a heat labile modification, for example, can be obtained by coupling citraconic anhydride or aconitric anhydride to the lysine residues of the enzyme. Enzymes carrying such modifications are meanwhile commercially available as Amplitaq Gold (Moretti, T., et al., Biotechniques 25 (1998) 716-22) or FastStart DNA polymerase (Roche Applied Sciences Cat No: 12 032 902 001). Addition of FastStart DNA polymerase as part of the "PCR reaction buffer" and subsequent activation during lysis step c) is shown herein to be a particularly efficient embodiment of the present disclosure.

Microtiter Plates Comprising a Dry Composition of PCR Reagents:

As disclosed herein, microtiter plates may be used for performing a method according to the present disclosure. In such embodiments, each vessel or reaction well of the microtiter plate may already comprise on its surface a dry composition of reagents which are subsequently required for PCR. The dry composition of the master mix is resolved by means of addition of the "PCR reaction buffer" in step b). In such embodiments, the "PCR reaction buffer" may not include any reagents which are part of the dry composition.

In the context of the present disclosure the phrase "dry composition" is used to emphasize that the amount of solvent, preferably of aqueous solvents is reduced below 5 weight %.

For example, such dry composition may comprise or only consist of a pair of amplification primers. Each well of a microtiter plate may comprise the same pair of amplification primers thereby enabling parallel analysis of multiple samples, or, substantially each well may comprise different pairs of amplification primers, thereby enabling a multiparametric analysis of one or only a few different samples. Of course, the plate layout can also be designed according to a mixture of the two concepts as well as for duplicate, triplicate or quadruplicate analysis. Methods for producing dry compositions of nucleic acids such as PCR amplification primers are well known in the art and include but are not limited to methods of freeze drying, lyophilisation or vacuum drying. For example, WO 2008/36544 describes the use of so-called filler materials in order to provide dried compositions, said filler materials include carbohydrates such as FICOLL™, sucrose, glucose, trehalose, melezitose, DEXTRAN™ and mannitol, proteins such BSA, gelatin or collagen and polymers such as PEG or polyvinyl pyrrolidone (PVP). Freeze-drying, as described in U.S. Pat. No. 5,593,824, for example, or vacuum drying, as described in U.S. Pat. No. 5,565,318, for example, have been disclosed for drying the biological materials in a carbohydrate polymer matrix.

In addition, such dry compositions may optionally comprise either at least one labeled hybridization probe or a double strand DNA binding fluorescent compound in order to enable real time PCR monitoring. Furthermore, said dried composition may additionally comprise a thermostable DNA polymerase and/or dNTPs.

Methods of producing dry compositions comprising proteins or enzymes are also disclosed in the art. Lyophilisation or freeze-drying is a well-established technique towards storage of proteins that is disclosed in the art (e.g. Passot, S., et al., Pharmaceutical Development and Technology 12 (2007) 543-553; Carpenter, J. F., et al., Pharmaceutical Research 14 (1997) 969-975; Schwegman, J. J., et al., Pharmaceutical Development and Technology 10 (2005) 151-173). For example, U.S. Pat. No. 7,407,747 discloses that a Taq polymerase can be dried in a mixture consisting of buffer solution, nucleotides, BSA and trehalose. Also, US 2010/0159529 discloses that the addition of an aptamer to the liquid solution enhanced the stability of the Taq polymerase, wherein said stabilization was good enough not only to dry, but also to store the dried mixture.

As will be understood by the skilled artisan, the disclosed method encompasses a number of variations. For example, if the dry composition comprises only amplification primers, a PCR master mix comprising the thermostable DNA Polymerase, dNTPs and all other PCR compounds necessary for amplification may be added as "PCR reaction buffer" during step b). Optionally either the "PCR reaction buffer" or the PCR master mix may in addition comprise a means for monitoring amplification in real time such as a fluorescently labeled hybridization probe, or, alternatively a fluorescent double strand DNA binding dye.

In another example, the dry composition may comprise all compounds necessary for PCR amplification (i.e., at least one pair of amplification primers, the thermostable DNA Polymerase, dNTPs and optionally at least one fluorescently labelled hybridization probe or fluorescent double strand DNA binding dye). In such embodiments, the "PCR reaction buffer" of step b) may be simply water, or, if necessary may comprise additional accessory compounds such as a pH buffering system (e.g., Tris salt), Mg2+salt and the like.

Kits According to the Present Disclosure:

The present disclosure also provides a new type of kits for performing real time PCR analysis. The kits comprise a reagent component and a disposable component, which together can be used and are specifically adapted for any of the methods disclosed above and exemplified herein.

Such kits comprise a plurality of reaction vessels designed to fit into a thermocycler instrument, and a PCR reaction buffer comprising a thermostable DNA polymerase. Such a kit for the first time provides to the scientist a useful tool containing a complete set of all reagents and disposables necessary for gene expression analysis.

In some embodiments, the reaction vessels may be physically connected with each other in a form of a microtiter plate. The microtiter plate may be a 96-384- or 1536-well microtiter plate, for example. Alternatively, said reaction vessels may be physically connected to each other in the form of a linear strip of a reaction vessel.

In some embodiments, said kit further comprises at least one pair of amplification primers, and optionally either at least one labeled hybridization probe or a double strand DNA binding fluorescent compound. These reagents may be stored within separate vessels and may be added to the PCR reaction buffer prior to the start of the experiment.

In alternative embodiments, said reaction vessels within said kit comprise a dry composition of at least one pair of PCR amplification primers and optionally either at least one labelled hybridization probe or a double strand DNA binding fluorescent compound.

The following examples, illustrative embodiments, and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

ILLUSTRATIVE EMBODIMENTS

The following comprises a list of illustrative embodiments according to the instant disclosure which represent various embodiments of the instant disclosure. These illustrative embodiments are not intended to be exhaustive or limit the disclosure to the precise forms disclosed, but rather, these illustrative embodiments are provided to aide in further describing the instant disclosure so that others skilled in the art may utilize their teachings.

1. A method for amplification of a target nucleic acid, comprising the steps of:
    a) transferring a liquid sample with a first volume comprising one or more living cells into a vessel,
    b) adding to said vessel a PCR reaction buffer with a second volume, whereas said second volume is at least 2× as large as said first volume,
    c) incubating said vessel for at least 30 seconds at at least 90° C.,
    d) amplifying said target by means of a polymerase chain reaction with a thermostable DNA polymerase without performance of an intermediate purification step,
    characterized in that steps a) to d) are performed within the same vessel.
2. The method of embodiment 1, characterized in that said vessel is a well of a microtiter plate.
3. The method of embodiment 2, characterized in that said vessel of said microtiter plate comprises a dry composition of PCR amplification primers, said composition optionally comprising either at least one labeled hybridization probe or a double strand DNA binding fluorescent compound.
4. The method of embodiment 3, characterized in that said dried composition additionally comprises a thermostable DNA polymerase and dNTPs.
5. The method of embodiment 1, characterized in that said vessel is a capillary or a tube of a stripe of reaction tubes.
6. The method of embodiments 1 thru 5, characterized in that prior to step a) said liquid sample comprising at least one or more living cells has been gained by a cell sorting method.
7. The method of embodiments 1 thru 6, wherein the ratio of the number of said living cells of step a) versus the liquid volume in which the polymerase chain reaction of step d) is performed is not greater than 2 cells/μl.
8. The method of embodiment 7, wherein said ratio is at least 1 cell/25 μl.
9. The method of embodiments 1 thru 8, wherein said target DNA is a single copy DNA.
10. A kit comprising:
    a plurality of reaction vessels designed to fit into a thermocycler instrument
    PCR reaction buffer comprising a thermostable DNA polymerase capable of performing PCR and dNTPs.
11. A kit according to embodiment 10, wherein said reaction vessels comprise a dry composition of at least one pair of PCR amplification primers and optionally either at least one labeled hybridization probe or a double strand DNA binding fluorescent compound.
12. A kit according to embodiments 10 thru 11, wherein said plurality of reaction vessels are physically connected with each other in a form of a microtiter plate or a linear strip of reaction vessels.
13. A kit according to embodiments 10 thru 12, wherein said thermostable polymerase is thermally activated by means of incubation for at least 1 minute at 90° C.

EXAMPLES

Example 1 qPCR for Amplification of the GAPDH Gene and the RPLI13A Gene from Sorted Mouse Hybridoma Cells A defined number of Mouse Hybridoma cells was deposited into separate wells of a 96 well microtiter plate using a Cell Sorter (Beckton Dickinson, FACS Aria I) in such a way that the liquid beam was always oriented into the center of the well. Due to the underlying technology of the Cell Sorter, however, it could not be excluded that a minor percentage of the sorted particles were not intact whole cells but cellular debris. Thus, in the following, the number of sorted material will be termed cell equivalent.

Cells sorted as disclosed were distributed into a 96 well microtiter plate (Roche Applied Science Cat. No: 04 729 692 001) designed for the LC480 real time PCR instrument (Roche Applied Science Cat. No: 05 015 278 001) according to the following pipetting scheme:
    1 cell equivalent/well of column 1-4
    2 cell equivalents/well in column 5-6
    4 cell equivalents/well in column 7-8
    8 cell equivalents/well in column 9
    16 cell equivalents/well in column 10
    32 cell equivalents/well in column 11
    64 cell equivalents/well in column 12
To each well, a master mix was added which contained:

```
0.4 µM Forward primer
                                        (SEQ ID NO: 1)
agcttgtcatcaacgggaag 0.4 µM Reverse primer
                                        (SEQ ID NO: 2)
tttgatgttagtggggtctcg 0.2 µM UPL Probe (Roche Applied Science Cat.
No: 04 685 075 001, No. 9)

1x LC480 Probe Master (Roche Applied Science
Cat. No: 04 902 343 001)
```

The forward and reverse primer were designed to amplify the mouse GAPDH gene, which is known to be present in the mouse genome in high copy numbers.

On a separate plate the same master mix was added, but primers and probe were designed to amplify the gene RPLI13A, which is present in only 12 copies of the mouse genome. Primers and probe were as follows:

```
0.4 µM Forward primer
                                        (SEQ ID NO: 3)
catgaggtcgggtggaagta 0.4 µM Reverse primer
                                        (SEQ ID NO: 4)
gcctgtttccgtaacctcaa
0.2 µM UPL Probe (Roche Applied Science Cat.
No: 04 686 993 001, No. 25)
```

The LightCycler Probe Master comprises the thermostable FastStart DNA polymerase, which is a hot start enzyme that is chemically modified. Activation is induced by means of removing said modification through incubation at high temperature.

qPCR was performed in an LC480 real time PCR instrument according to the following thermocycling protocol:

| | | | |
|---|---|---|---|
| Preincubation: | 1x | 95° C. | 10' |
| Denaturation | 45x | 95° C. | 10" |
| Annealing | 45x | 60° C. | 30" |
| Elongation | 45x | 72° C. | 1" |
| Cooling ramp rates | | 2.2° C./s | |
| Heating ramp rates | | 4.4° C./s | |

Detection of amplification signals and calculation of cp values (low cp values indicating a high level of amplification) was performed according to the instructions of the Manufacturer's manuals.

The following table discloses the average cp values obtained for the different cell equivalent numbers per well analyzed:

| Number of cells | Average cp Value | |
|---|---|---|
| | GAPDH | RPLI13A |
| 1 | 33.00 | 36.10 |
| 2 | 31.40 | 34.00 |
| 4 | 31.28 | 33.92 |
| 8 | 29.38 | 33.35 |
| 16 | 29.02 | 31.67 |
| 32 | 28.46 | 31.37 |
| 64 | 28.29 | 30.99 |

As can be seen from the table, signals originating from the high copy number mouse GAPDH gene as well as the RPLI13A gene, which is present in 12 copies in the mouse genome, can be detected even if only 1 cell is used as a starting material.

Moreover, it can be observed that the cp values inversely correlate with the number of cells/per well. Thus, it can be obviously concluded that addition of the PCR reaction buffer and subsequent incubation for 10' at 95° C. was obviously enough to lyse the cells in a quantitative manner.

Example 2 qPCR for Amplification of the Kcnj2 Gene from Sorted Mouse Hybridoma Cells

The experiment was essentially carried out as disclosed for example 1 with the alteration that primers and probe were designed to amplify the single copy mouse gene Kcnj2. Primers and probe were as follows:

```
Forward primer
                                    (SEQ ID NO: 5)
ctgtcttgccttcgtgctct Reverse primer
                                    (SEQ ID NO: 6)
agcagggctatcaaccaaaa
UPL Probe (RocheApplied Science Cat.
No: 04 688 996 001, No. 76)
```

The table discloses the average cp values obtained for the different cell equivalent numbers per well analyzed:

| Number of cells | Average cp value |
|---|---|
| 1 | 38.31 |
| 2 | 36.64 |
| 4 | 36.26 |
| 8 | 36.10 |
| 16 | 33.93 |
| 32 | 32.88 |
| 64 | 34.03 |

As can be seen from the table, amplification signals originating from the single copy number mouse gene Kcnj2 can be obtained, even if only one cell is used as a starting material. In other words, the present disclosure provides a solution for amplification of single copy genes from single cell samples.

Moreover, it can be observed that the cp value increases, if the sample originates from a higher cell number such as 64 cells. This can be explained by the fact that due to the lysis within the PCR reaction buffer at 95° C., the concentration of cell debris within the given reaction volume increases and thus may inhibit amplification efficiency of the PCR reaction. It can be concluded that the present disclosures is especially applicable for PCR on samples originating from lower cell numbers.

Furthermore, the following table discloses the cp values obtained from individual single cell samples:

| | | | | | | | |
|---|---|---|---|---|---|---|---|
| 40.00 | 36.96 | 36.71 | 35.92 | — | 40.00 | — | — |
| 37.71 | 40.00 | — | 40.00 | 39.56 | 37.19 | 37.22 | 38.50 |

As it can be deduced from the table, no amplification signals were obtained in about 4 out of 16 parallel reactions. Taking the results of example 2 into account, which proves that not every single sorting event results in the actual separation and delivery of a single cell into a reaction vessel this result is explainable. In other words, the fact that in some cases no amplification signal is observed is due to the fact that the individual wells did not contain a cell, but it is not due to the fact that the lysis and amplification procedure itself has a certain failure rate.

Example 3 qPCR for Amplification of the Kcnj2 Gene from Sorted Mouse Hybridoma Cells Using Microtiter Plates Containing Dried Reagents The experiment was essentially performed as disclosed for example 2 with the following alterations: 10 µl of a solution containing the required primers and probe was filled into each well of a microtiter plate. The microtiter plate was incubated for 12 h at 25° C. and 200 mBar, and subsequently for 4 h at 25° C. and 50 mBar, so that the primers and probes were dried onto the surface of each reaction well of the microtiter plate.

Subsequently, cell deposition was performed as follows:

1 cell equivalent/well of column 1-6
2 cell equivalents/well in column 7
4 cell equivalents/well in column 8
8 cell equivalents/well in column 9
16 cell equivalents/well in column 10
32 cell equivalents/well in column 11
64 cell equivalents/well in column 12

After addition of 20 µl master mix, the real time PCR analysis was performed. The table discloses the average cp values obtained for the different cell numbers analyzed:

| Number of cells | Average cp value |
|---|---|
| 1 | 38.14 |
| 2 | 37.45 |
| 4 | 36.22 |
| 8 | 35.14 |
| 16 | 34.89 |
| 32 | 33.76 |
| 64 | 33.27 |

It is also important to note that from the 48 wells used for single cell analysis, only 10 amplification reactions were negative. These reactions were not included into the calculation of the average cp value.

Example 4 qPCR for Amplification of the Kcnj2 Gene from Single Mouse Hybridoma Cells Using Microtiter Plates Containing Dried Reagents In order to analyze, how much percentage of cell equivalent actually corresponds to a living cell rather than to cellular debris, 3×30 sorted equivalents were deposited each on a microscopic slide and counted. 28, 28 and 29 cells, respectively could be identified by visual inspection through a microscope. This corresponds to 94% living cells versus 6% cellular debris per cell equivalent (sorting event).

In the following the experiment was essentially performed on two microtiter plates as disclosed for example 3 with the alteration, that on both microtiter plates, each reaction well only contained a single cell equivalent. Results were as follows:

| Plate No. | Number of wells without detectable amplification | Percentage of wells with detectable amplification | Average cp value of wells with detectable amplification | Standard deviation cp value |
|---|---|---|---|---|
| 1 | 16/96 | 84% | 38.85 | 1.14 |
| 2 | 5/96 | 95% | 38.31 | 1.01 |

The results show that it is possible to perform single cell analysis according to the PCR method as provided by the present disclosure. Moreover, also if single cell analysis is intended, the primers and probe are dried onto the surface of the microtiter plate.

Example 5

1-step-RT-PCR for Detection of the ActB, and B2M and 1 Expression

Cells were sorted and disposed on a microtiter plate as disclosed in example 1, resulting in sample volume of less than 2 µl.

To each well, a 1×LC480 RNA Master Hydrolysis probes (Roche Applied Science Cat. No. 04 991 885 001, containing T.th polymerase and a hot start aptamer) was added.

The master mix in addition contained the following primers and probes:

Row 1-2: 1-step RT-PCR of ActB
0.4 µM Forward primer
(SEQ ID NO: 7)
AAGGCCAACCGTGAAAAGAT
0.4 µM Reverse primer
(SEQ ID NO: 8)
GTGGTACGACCAGAGGCATAC
0.2 µM UPL Probe (Roche Applied Science Cat. No: 56)

Row 3-4: 1-step RT-PCR of B2M
0.4 µM Forward primer
(SEQ ID NO: 9)
TACGCCTGCAGAGTTAAGCA
0.4 µM Reverse primer
(SEQ ID NO: 10)
GGTTCAAATGAATCTTCAGAGCA
0.2 µM UPL Probe (Roche Applied Science Cat. No: 117)

Row 5-6: 1-step RT-PCR of 18s RNA
0.4 µM Forward primer
(SEQ ID NO: 11)
GCCGCTAGAGGTGAAATTCTT
0.4 µM Reverse primer
(SEQ ID NO: 12)
CGTCTTCGAACCTCCGACT 0.2 µM UPL Probe (Roche Applied Science Cat. No: 93)

On a first plate, 1-step-RT-PCR was performed in an LC480 real time PCR instrument according to the following thermocycling protocol:

| Preincubation: | 1x | 95° C. | 30" |
|---|---|---|---|
| Denaturation | 45x | 95° C. | 10" |
| Annealing | 45x | 60° C. | 30" |
| Elongation | 45x | 72° C. | 1" |
| Cooling ramp rates | | 2.2° C./s | |
| Heating ramp rates | | 4.4° C./s | |

On a second plate, 1-step-RT-PCR was performed in an LC480 real time PCR instrument according to a thermocycling protocol including a further preincubation step at 61° C.

| Preincubation: | 1x | 61° C. | 3" |
|---|---|---|---|
| Preincubation: | 1x | 95° C. | 30" |
| Denaturation | 45x | 95° C. | 10" |
| Annealing | 45x | 60° C. | 30" |
| Elongation | 45x | 72° C. | 1" |
| Cooling ramp rates | | 2.2° C./s | |
| Heating ramp rates | | 4.4° C./s | |

Detection of amplification signals and calculation of cp values (low cp values indicating a high level of amplification) was performed according to the instructions of the Manufacturer's manuals.

In order to prove that the measured cp values actually reflect the detection of mRNA expression rather than DNA, the correct size of the amplicons was subsequently confirmed by means gel electrophoresis. The following table discloses the average cp values obtained for the different cell numbers analyzed.

| Target/ | Without preincubation at 61° C. | | With preincubation at 61° C. | |
|---|---|---|---|---|
| Number of cells | MeanCp | STD Cp | MeanCp | STD Cp |
| Actb/1 | 32.06 | 0.60 | 30.55 | 0.35 |
| Actb/2 | 31.60 | 1.12 | 29.12 | 0.50 |
| Actb/4 | 31.15 | 0.71 | 28.71 | 0.47 |
| Actb/8 | 29.92 | 0.11 | 27.78 | 0.07 |
| Actb/16 | 29.13 | 0.30 | 27.05 | 0.39 |
| Actb/32 | 28.24 | 0.22 | 25.98 | 0.23 |
| Actb/64 | 26.47 | 0.13 | 24.11 | 0.01 |
| B2M/1 | 36.04 | 0.38 | 31.64 | 0.00 |
| B2M/2 | 36.13 | 0.43 | 30.99 | 0.06 |
| B2M/4 | 35.54 | 0.24 | 30.88 | 0.22 |
| B2M/8 | 34.64 | 0.48 | 30.69 | 0.25 |
| B2M/16 | 34.52 | 0.01 | 30.21 | 0.13 |
| B2M/32 | 34.19 | 0.13 | 30.15 | 0.08 |
| B2M/64 | 34.59 | 0.07 | 30.13 | 0.10 |
| 18s/1 | 27.90 | 0.55 | 24.43 | 1.36 |
| 18s/2 | 27.27 | 0.32 | 23.59 | 0.74 |
| 18s/4 | 26.81 | 0.44 | 22.43 | 0.57 |
| 18s/8 | 25.74 | 0.19 | 22.49 | 0.21 |
| 18s/16 | 25.21 | 0.49 | 21.62 | 0.16 |
| 18s/32 | 24.66 | 0.18 | 20.78 | 0.25 |
| 18s/64 | 23.44 | 0.06 | 19.38 | 0.03 |

As can be seen from the table, expression of the genes tested can be detected in material originating from only one cell used as a starting material. It can be observed that the cp values inversely correlate with the number of cells/per well. The reverse transcription step takes place during the initial ramping, annealing and elongation steps of the thermocycling protocol.

As can be further deducted from the table, surprisingly the detection of expression is even more sensitive, in case of a preincubation step for 3 minutes at 61° C. prior to the actual lysis at 95° C. Probably such a positive effect is due to the small sample volume of less than 2 µl, which results in an immediate drying and destruction of the few sorted cells, such that the cellular RNA becomes available for the reverse transcription reaction.

Example 6

Comparison Between DNA PCR and 1-Step-RT-PCR on the 18s Target

Cells were sorted and disposed on a microtiter plate as disclosed in example 1 according to the following pipetting scheme:

For 3 identical plates No 1-3, 1×LC480 RNA Master Hydrolysis probes (Roche Applied Science Cat. No 04 991 885 001, containing T.th polymerase and a hot start aptamer) was added in order to amplify an RNA with a 1-step-RT PCR reaction. Primers were designed in such a way that during this reaction, both the RNA and its corresponding genomic DNA fragment were amplifiable. For a fourth plate No 4, a Real Time ready DNA probes master (Roche Applied Science Cat. No: 05 502 381 001) comprising a thermostable DNA dependent DNA Polymerase without any reverse transcriptase activity was used.

In addition the 4 set ups contained the following primers and probes suitable for amplification of 18s RNA and DNA:

```
0.4 µM Forward primer
                                        (SEQ ID NO: 11)
GCCGCTAGAGGTGAAATTCTT 0.4 µM Reverse primer
                                        (SEQ ID NO: 12)
CGTCTTCGAACCTCCGACT
0.2 µM UPL Probe (Roche Applied Science Cat.
No: 93)
```

For Plate 1, 1-step-RTPCR was performed with a preincubation step at 61° C. in an LC480 real time PCR instrument according to the following thermocycling protocol:

| Predenaturation: | 1x | 95° C. | 1' |
|---|---|---|---|
| Preincubation: | 1x | 61° C. | 3' |
| Preincubation: | 1x | 95° C. | 30" |
| Denaturation | 45x | 95° C. | 10" |
| Annealing | 45x | 60° C. | 30" |
| Elongation | 45x | 72° C. | 1" |
| Cooling ramp rates | | 2.2° C./s | |
| Heating ramp rates | | 4.4° C./s | |

For plate 2 and 3, RT-PCR was performed without any preincubation at 61° C.:

| Preincubation: | 1x | 95° C. | 30" (plate 2) or 2' (plate 3) |
|---|---|---|---|
| Denaturation | 45x | 95° C. | 10" |
| Annealing | 45x | 60° C. | 30" |
| Elongation | 45x | 72° C. | 1" |
| Cooling ramp rates | | 2.2° C./s | |
| Heating ramp rates | | 4.4° C./s | |

The same protocol as for plate 3 was used for plate 4 in order to perform a PCR without any reverse transcription activity.

Detection of amplification signals and calculation of cp values (low cp values indicating a high level of amplification) was performed according to the instructions of the Manufacturer's manuals.

In order to prove that the measured cp values actually reflect the detection of mRNA expression rather than DNA, the correct size of the amplicons was subsequently confirmed by means gel electrophoresis. The following table discloses the average cp values obtained for the different cell numbers analyzed.

| | Plate 1 RT-PCR | | Plate 2 RT-PCR without RT step With 30" preincubation | | Plate 3 RT-PCR without RT step With 2' preincubation | | Plate 4 PCR | |
|---|---|---|---|---|---|---|---|---|
| No of cells | MeanCp | STD Cp | MeanCp | STD Cp | MeanCp | STD Cp | MeanCp | STD Cp |
| 1 | 25.24 | 1.11 | 27.90 | 0.55 | 29.13 | 0.70 | 34.18 | 0.68 |
| 2 | 23.97 | 0.54 | 27.27 | 0.32 | 28.48 | 0.47 | 32.99 | 0.41 |
| 4 | 23.74 | 0.86 | 26.81 | 0.44 | 27.67 | 0.17 | 31.98 | 0.38 |
| 8 | 22.48 | 0.14 | 25.74 | 0.19 | 26.95 | 0.21 | 30.93 | 0.23 |

-continued

| | Plate 1 RT-PCR | | Plate 2 RT-PCR without RT step With 30" preincubation | | Plate 3 RT-PCR without RT step With 2' preincubation | | Plate 4 PCR | |
|---|---|---|---|---|---|---|---|---|
| No of cells | MeanCp | STD Cp | MeanCp | STD Cp | MeanCp | STD Cp | MeanCp | STD Cp |
| 16 | 21.82 | 0.14 | 25.21 | 0.49 | 25.63 | 0.15 | 29.05 | 0.36 |
| 32 | 19.92 | 0.12 | 24.66 | 0.18 | 25.18 | 0.26 | 28.16 | 0.04 |
| 64 | 18.89 | 0.01 | 23.44 | 0.06 | 23.87 | 0.05 | 27.60 | 0.33 |

As can be seen from the table, the results from the RT-PCR provide lower cp values as compared to results from the corresponding PCR reactions. This is indicative for a higher starting concentration of target nucleic acid, which according to the conditions as chosen results from amplification of both the respective RNA and its corresponding gene sequence within the RT-PCR set up.

When the RT-PCR results with 3 minutes at 61° C. and no preincubation at 61° C. are compared, it is obvious that a preincubation is not necessary but results in an increased sensitivity of RNA detection. As disclosed in example 5 the latter observed effect may be due to the small sample volume of less than 2 μl, which results in an immediate drying and destruction of the few sorted cells, such that the cellular RNA becomes available for the reverse transcription reaction.

All references cited in this specification are herewith incorporated by reference with respect to their entire disclosure content and the disclosure content specifically mentioned in this specification.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. A method of amplifying a target nucleic acid within a liquid sample, comprising the steps of:
   a) transferring the liquid sample comprising one or more living cells comprising the target nucleic acid into a vessel, the liquid sample having a first volume;
   b) adding a PCR reaction buffer having a second volume to the vessel, the second volume being at least two times as large as the first volume;
   c) incubating the vessel for at least 30 seconds at at least 90° C.; and
   d) amplifying the target nucleic acid by means of a polymerase chain reaction with a thermostable DNA polymerase, said step of amplifying occurring without performance of an intermediate purification step following said step of incubating, and said steps of transferring, adding, incubating and amplifying being performed within the same vessel.

2. The method of claim 1, wherein the vessel is a well of a microtiter plate.

3. The method of claim 2, wherein the well of the microtiter plate comprises a dry composition of PCR amplification primers.

4. The method of claim 3, wherein the dry composition further comprises one of a labeled hybridization probe and a double strand DNA binding fluorescent compound.

5. The method of claim 3, wherein the dry composition further comprises the thermostable DNA polymerase and a plurality of dNTPs.

6. The method of claim 1, wherein the vessel is one of a capillary and a tube of a strip of reaction tubes.

7. The method of claim 1 further comprising the step of subjecting the liquid sample to a cell sorting method prior to said step of transferring.

8. The method of claim 1, wherein the living cells of said step of transferring comprise a ratio, in comparison to a volume in which the polymerase chain reaction of said step of amplifying is performed, of not greater than 2 cells/µl.

9. The method of claim 8, wherein the ratio is at least 1 cell/25 µl.

10. The method of claim 1, wherein said target nucleic acid is a single copy DNA.

11. The method of claim 1, wherein the thermostable DNA polymerase is a DNA dependent DNA polymerase.

12. The method of claim 1, wherein the PCR reaction buffer of said step of adding comprises a pair of amplification primers, the thermostable DNA polymerase and a plurality of dNTPs.

13. The method of claim 1, wherein the thermostable DNA polymerase is configured to become activated during said step of incubating.

14. The method of claim 13, wherein the thermostable DNA polymerase comprises a chemical modification which is removed during said step of incubating.

* * * * *